(12) United States Patent
Novak et al.

(10) Patent No.: US 9,693,792 B2
(45) Date of Patent: Jul. 4, 2017

(54) ULTRASONIC TREATMENT METHOD AND APPARATUS WITH ACTIVE PAIN SUPPRESSION

(75) Inventors: Theodore A. D. Novak, Northport, NY (US); Ronald R. Manna, Valley Stream, NY (US)

(73) Assignee: MISONIX, INCORPORATED, Farmingdale, NY (US)

(*) Notice: Subject to any disclaimer, the term of this patent is extended or adjusted under 35 U.S.C. 154(b) by 2977 days.

(21) Appl. No.: 11/582,746

(22) Filed: Oct. 18, 2006

(65) Prior Publication Data

US 2008/0146921 A1    Jun. 19, 2008

(51) Int. Cl.
*A61N 1/36* (2006.01)
*A61B 17/32* (2006.01)

(52) U.S. Cl.
CPC .. *A61B 17/320068* (2013.01); *A61N 1/36021* (2013.01)

(58) Field of Classification Search
USPC ....... 600/437, 439; 606/29, 30; 607/2–3, 33; 601/2–4
See application file for complete search history.

(56) References Cited

U.S. PATENT DOCUMENTS

| | | | |
|---|---|---|---|
| 6,648,839 B2 | 11/2003 | Manna | |
| 6,896,672 B1* | 5/2005 | Eggers et al. | 606/32 |
| 7,165,451 B1* | 1/2007 | Brooks et al. | 73/579 |
| 2002/0193784 A1* | 12/2002 | McHale et al. | 606/27 |
| 2006/0167500 A1* | 7/2006 | Towe et al. | 607/3 |
| 2008/0015473 A1* | 1/2008 | Shimizu | 601/2 |

* cited by examiner

*Primary Examiner* — Christopher Cook
(74) *Attorney, Agent, or Firm* — R. Neil Sudol; Henry D. Coleman

(57) ABSTRACT

An ultrasonic medical treatment device has a probe, a transducer for mechanically vibrating the probe at an ultrasonic frequency, a voltage source for energizing the transducer, and another electrical voltage source for feeding to the probe a high-frequency alternating waveform of limited current and limited voltage to be conducted into a patient through the operative tip of the probe after placement of the operative tip into contact with the patient. The alternating waveform has a current and a voltage so limited as to prevent damage to organic tissues while stimulating nerves to reduce or suppress pain.

8 Claims, 3 Drawing Sheets

ULTRASONIC TREATMENT METHOD AND APPARATUS WITH ACTIVE PAIN SUPPRESSION

BACKGROUND OF THE INVENTION

This invention relates to ultrasonic surgical instruments and associated methods of use. More particularly, this invention relates to the treatment of wounds with ultrasound energy. The treatment contemplated by this invention includes fragmentation and emulsification of hard and soft tissue in a clinical environment while reducing unwanted heat and collateral tissue damage. In addition, the treatment includes method and apparatus for reducing pain at the operative site without drugs or other systemic treatment such as anesthesia. The present invention may be used in the treatment of wounds, warts or other lesions, wrinkles or skin disease.

Over the past 30 years, several ultrasonic tools have been invented which can be used to ablate or cut tissue in surgery. Such devices are disclosed by Wuchinich et al. in U.S. Pat. No. 4,223,676 and Idemoto et al in U.S. Pat. No. 5,188,102.

In practice, these surgical devices include a blunt tip hollow probe that vibrates at frequencies between 20 kc and 100 kc, with amplitudes up to 300 microns or more. Such devices ablate tissue by either producing cavitation bubbles which implode and disrupt cells, by generating tissue compression and relaxation stresses (sometimes called the jackhammer effect) or by other mechanisms such as micro streaming of bubbles in the tissue matrix. The effect is that the tissue becomes liquefied and separated. The fragmented tissue becomes emulsified with an irrigant solution. The resulting emulsion or slurry of tissue debris is then aspirated from the site. Bulk excision of tissue is possible by applying the energy around and under an unwanted tissue mass to separate it from the surrounding structure. The surgeon can then lift the separated tissue mass out using common tools such as forceps.

The tubular probe is excited by a transducer of either the piezoelectric or magnetostrictive type that transforms an alternating electrical signal within the frequencies indicated above into a longitudinal or transverse vibration. When the probe is attached to the transducer, the two become a single element with series and parallel resonances. The designer will try to tailor the mechanical and electrical characteristics of these elements to provide the proper frequency of operation. Most of the time, the elements will have a long axis that is straight and has the tip truncated in a plane perpendicular to the long axis, as shown in FIG. 1. This is done for simplicity and economic considerations. In almost all applications, whether medical or industrial, such an embodiment is practical and useful. However, in applications such as the debridement of burns, wounds, diabetic ulcers or ulcers induced by radiation treatments, the blunt straight probe has been shown to be less effective in removing the hard eschar buildup that occurs when the wound is healing. This eschar buildup must be removed so that the healthy tissue is exposed and allowed to close the wound to provide complete healing with minimal scar tissue formation. Also, the small diameter tip, since it is cannulated, has a small annular area with limits energy transmission into the wound. This extends the length of the procedure and causes operator fatigue and patient discomfort.

Therefore, it was desired to provide a probe that can be mated to an ultrasonic surgical aspirator that increases the efficiency of emulsification, does not heat up the operative site and lowers the time of operation.

In response to this need, a series of devices were developed which have been proven to address all of the shortcomings of the prior art and eliminate them. These devices are described in commonly owned copending U.S. application Ser. No. 11/087,451, filed Mar. 23, 2005. The devices have been shown to be effective in clinical use for the removal of necrotic tissue and hard eschar. The methods described in that prior application have also been shown to be efficacious in this regard.

However, the devices need to be driven at high excursion levels, i.e., high vibrational amplitudes in order to effectively remove unwanted tissue. Once this tissue is removed, the high amplitudes can lead to higher pain perception on the part of the patient and can also lead to destruction of viable tissue if the operator is not careful. Also, the wound healing rates have been shown to be roughly the same as is observed after standard sharps debridement. An improvement in the healing rate that manifests itself as shorter time to heal is desired.

Although the devices of the previous applications have gone a long way to reduce operative pain, some patients are extremely sensitive to any ultrasound activity and are not candidates for ultrasound treatment, regardless of the proven clinical benefits. Therefore, a need exists for a device that incorporates an intrinsic pain blocking or masking function, in order to reduce pain at the site and provide relief to the patient during treatment.

OBJECTS OF THE INVENTION

An object of the present invention is to provide an improved ultrasonic surgical instrument.

An associated object of the present invention is to provide an improved ultrasonic surgical instrument for use in debridement of wounds, removal of warts or other lesions or any dermatological treatment.

A more specific object of the present invention is to provide an improved ultrasonic surgical instrument that enhances surgical efficiency and reduces the pain sensation of the patient.

A related object of the present invention is to provide an ultrasonic treatment method utilizable in wound debridement, which reduces the pain sensation of the patient.

These and other objects of the invention will be apparent from the drawings and descriptions herein. Although every object of the invention is attained in at least one embodiment of the invention, there is not necessarily any embodiment which attains all of the objects of the invention.

SUMMARY OF THE INVENTION

A medical treatment device comprises, in accordance with the present invention, (1) an ultrasonic probe, (2) a transducer assembly operatively connected to the probe for mechanically vibrating the probe so that an operative tip of the probe oscillates at an ultrasonic frequency, (3) a first electrical voltage source operatively connected to the transducer assembly for energizing same with an alternating voltage having an ultrasonic frequency, and (4) a second electrical voltage source operatively connected to the probe for feeding thereto a high-frequency alternating waveform of limited current and limited voltage to be conducted into a patient through the operative tip of the probe after placement of the operative tip into contact with the patient. The alternating waveform has a current and a voltage (or power output) so limited as to prevent damage to organic tissues while stimulating nerves to reduce or suppress pain. The current and voltage parameters are identical to or substantially the same as those of currently used transcutaneous electrical nerve stimulation (TENS) devices.

Pursuant to another feature of the present invention, the medical treatment device further comprises a synchronization circuit operatively connected to at least one of the first electrical voltage source and the second electrical voltage source for synchronizing the vibrating of the probe with the conducting of the alternating waveform into the patient via the probe. The synchronization circuit may include an enabling circuit component operatively connected to the first electrical voltage source for enabling a vibrating of the probe only within a predetermined time interval of a conducting of the alternating waveform into the patient.

The enabling circuit component may more particularly include a time delay element for enabling a commencing of probe vibration only after a predetermined time period has elapsed after a conducting of the alternating waveform into the patient has commenced. Pursuant to a further feature of the present invention, the enabling circuit component further includes a detector operatively connected to the delay element. The detector is operatively connected to at least one of the probe and the second electrical voltage source for sensing when a conducting of the alternating waveform into the patient via the probe has commenced.

The alternating waveform may have a frequency between approximately 70 MHz and 100 MHz. The second electrical voltage source may include a circuit for pulsing the alternating waveform.

A medical treatment method comprises, in accordance with the present invention, (a) contacting a patient with an operative tip of an ultrasonic probe, (b) conducting a high-frequency alternating voltage into the patient through the operative tip of the probe while the operative tip is in contact with the patient, and (c) mechanically vibrating the probe so that the operative tip oscillates at an ultrasonic frequency while the operative tip is in contact with the patient.

The method may additionally comprise synchronizing the vibrating of the probe with the conducting of the alternating voltage into the patient via the probe. The synchronizing may include enabling a vibrating of the probe only within a predetermined time interval of a conducting of the alternating voltage into the patient. The enabling may in turn include commencing probe vibration only after a predetermined time period has elapsed after a conducting of the alternating voltage into the patient has commenced.

According to another aspect of the present invention, the enabling of probe vibration includes automatically detecting when a conducting of the alternating voltage into the patient via the probe has commenced.

In the method of the present invention, the conducting of the alternating voltage may include pulsing the alternating voltage. The alternating voltage may have a frequency between approximately 70 MHz and 100 MHz.

DETAILED DESCRIPTION

Figure 1:
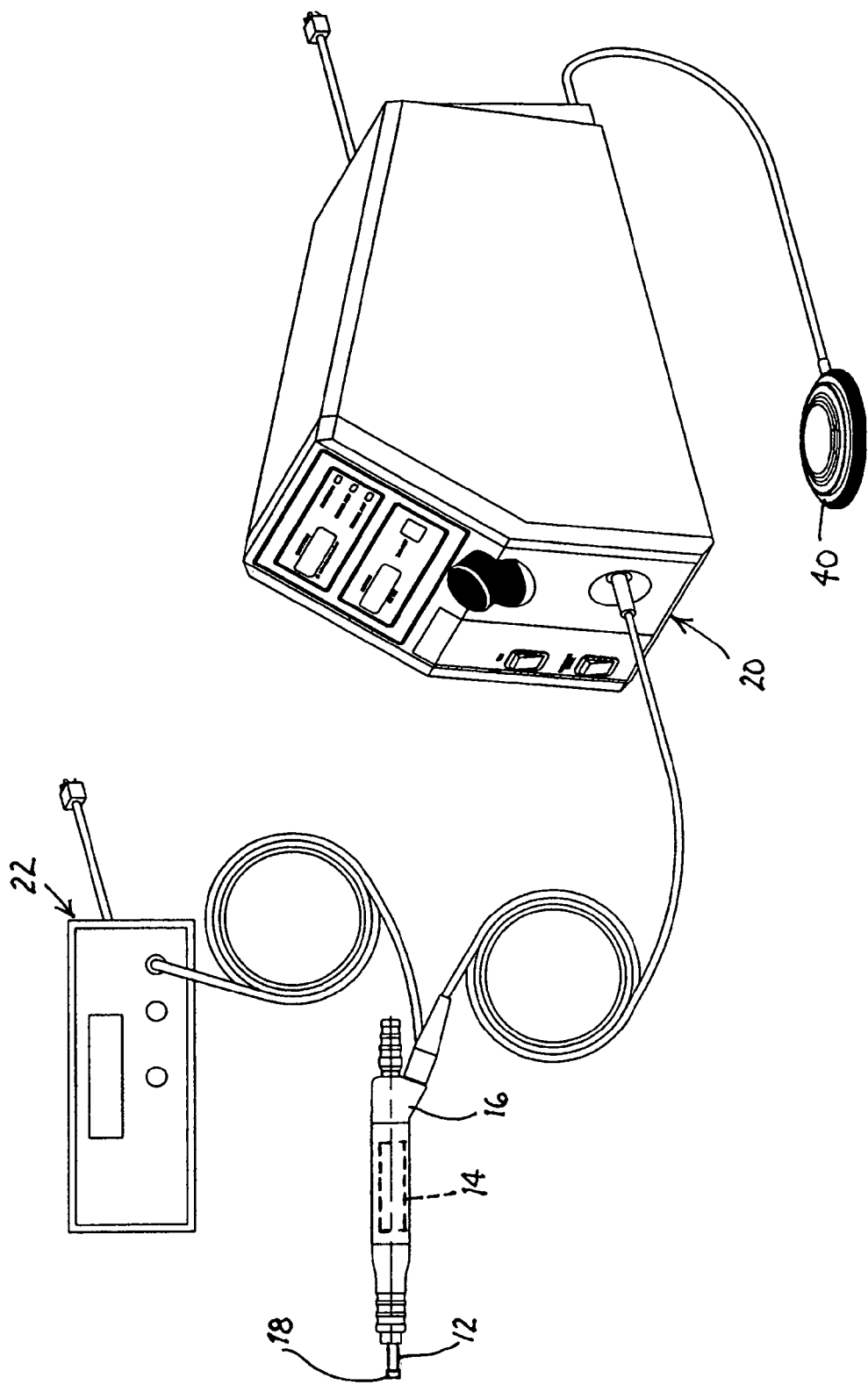
FIG. 1 is partially a schematic perspective vie and partially an elevational view of a medical treatment device or system in accordance with the present invention.

As depicted in FIG. 1, a medical treatment device comprises an ultrasonic probe 12 operatively connected to a transducer assembly 14 in a handpiece 16 for receiving therefrom mechanical vibratory energy so that an operative tip 18 of the probe oscillates at an ultrasonic frequency suitable for performing a surgical procedure such as wound abrasion or other removal of organic tissues. A first electrical voltage source or generator 20 is operatively connected to transducer assembly 14 for energizing the assembly with an alternating voltage having an ultrasonic frequency. A second electrical voltage source or generator 22 operatively connected to probe 12 for feeding thereto a high-frequency alternating waveform of limited current and limited voltage to be conducted into a patient through the operative tip 18 of the probe after placement of the operative tip into contact with the patient. The alternating waveform produced by source 22 has a current and a voltage (or power output) so limited as to prevent damage to organic tissues of the patient while stimulating nerves to reduce or suppress pain. The current and voltage parameters are substantially the same as those of known transcutaneous electrical nerve stimulation (TENS) devices.

Figure 2:
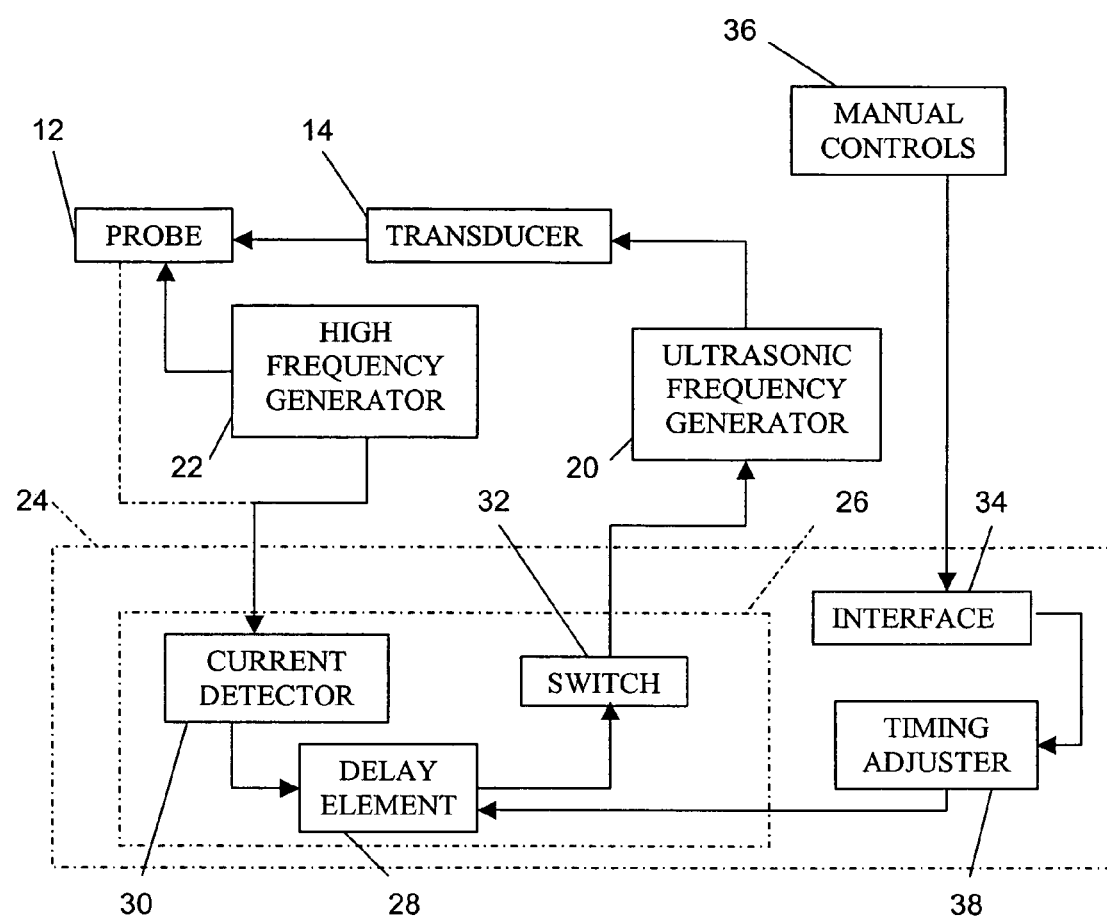
FIG. 2 is a block diagram of functional components of the device or system of FIG. 1.

As shown in FIG. 2, the medical treatment device further comprises a synchronization circuit 24 operatively connected to voltage sources 20 and 22 for synchronizing the vibrating of probe 12 with the conducting of the alternating waveform into the patient via the probe. Synchronization circuit 24 includes an enabling circuit 26 operatively connected to voltage source 20 for enabling a vibrating of probe 12 only within a predetermined time interval of a conducting of the alternating waveform from source 22 into the patient.

Enabling circuit 26 includes a time delay element 28 for enabling a commencing of probe vibration only after a predetermined time period has elapsed after a conducting of the alternating waveform into the patient has commenced. Enabling circuit 26 further includes a detector 30 operatively connected to delay element 28. Detector 30 may take the form of a current sensor operatively connected to probe 12 and/or voltage source 22 for sensing when a conducting of the alternating waveform into the patient via the probe has commenced.

Figure 3:
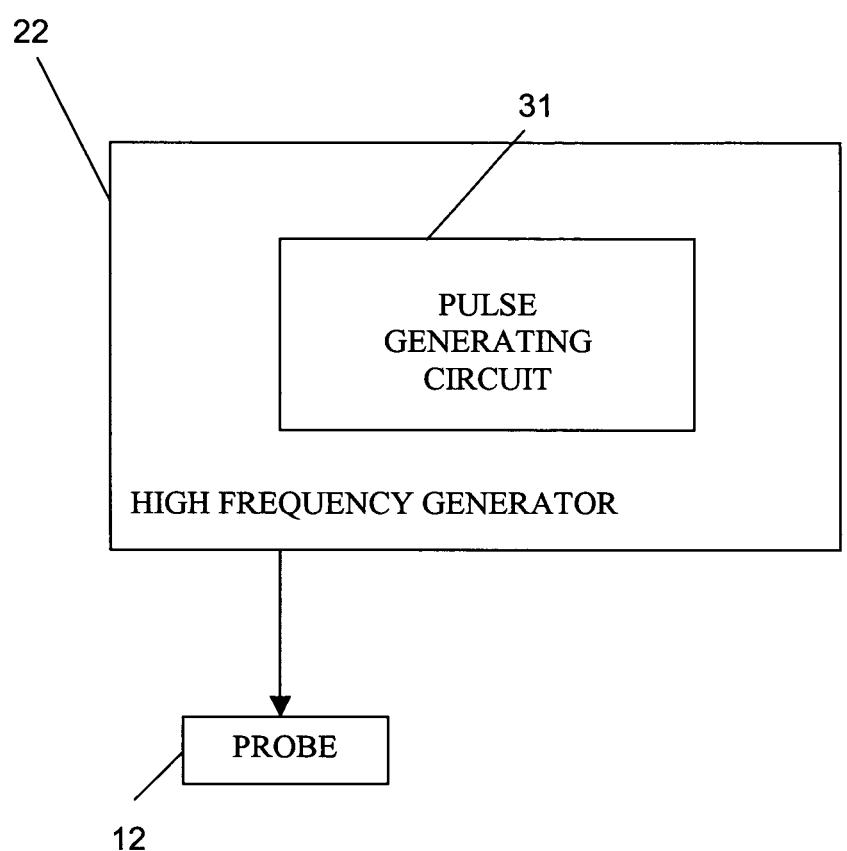
FIG. 3 is a block diagram of a high-frequency generator shown in FIG. 2

The alternating waveform has a frequency between approximately 70 MHz and 100 MHz. Voltage source 22 may include a circuit 31 (FIG. 3) for pulsing the alternating waveform.

As further shown in FIG. 2, enabling circuit 26 includes a switch 32 such as a logic gate or transistor operating connected on an input side to delay element 28 and on an output side to voltage source 20 for activating source 20.

Enabling circuit 26 may also function to disable or interrupt the generation of the alternating voltage by source 20 and concomitantly the vibration of probe tip 18 within a predetermined time interval after the termination of the TENS operation of source 22. Where voltage source 22 includes pulsing, this time interval for inducing the deactivation or interruption of voltage source 20 is longer than the inter-pulse interval between successive periods of conduction of the alternating TENS waveform from source or generator 22 to probe 12.

Synchronization circuit 24 includes an interface 34 operatively connected on an input side to one or more manual controls 36 and on an output side to an adjustment module 38, also a part of synchronization circuit 24. In response to operator instructions entered via controls 36 and identified and decoded by interface 34, adjustment module 38 transmits a signal to detector 30 and/or delay element 28 to modify, for instance, the length of the delay between the beginning of TENS current application and the start of probe tip vibration.

In using the treatment apparatus of FIGS. 1 and 2, a surgeon manipulates handpiece 16 to place probe tip 18 into contact with a patient at a surgical site. Voltage source 22 is operated to generate the high frequency alternating TENS waveform, which is conducted into the patient through probe tip 18 while the probe tip is in contact with the patient. Either simultaneously with or subsequently to the commencement of TENS current conduction, source 20 is activated to energize transducer assembly 14 for generating, in probe 12, a standing mechanical compression wave having an ultrasonic frequency, Operative tip 18, typically located at an anti-node of the standing compression wave, vibrates at the ultrasonic frequency.

Pursuant to the embodiment of the ultrasonic treatment device shown in FIGS. 1 and 2, ultrasonic vibration commences automatically in predetermined synchronization with the conduction of TENS current. Similarly, the termination or interruption of probe tip vibration occurs automatically. It is possible, however, for at least the commencement of probe tip vibration to be under operator control. To that end, switch 32 may be connected to an alert signal generator (not shown) such as an electromechanical transducer for producing an audible acoustic pressure wave. The generation of a sensible alert signal serves to prompt the operator to activate source 20 and commence ultrasonic treatment of organic tissues at a surgical site.

As depicted in FIG. 1, a footswitch 40 may be provided. In the apparatus of FIGS. 1 and 2, a depression of footswitch 40 activates voltage source 22 and, simultaneously or subsequently, voltage source 20.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A medical treatment device comprising:
    an ultrasonic probe;
    a transducer assembly operatively connected to said probe for mechanically vibrating said probe so that an operative tip of said probe oscillates at an ultrasonic frequency;
    a first electrical voltage source operatively connected to said transducer assembly for energizing same with an alternating voltage having an ultrasonic frequency;
    a second electrical voltage source operatively connected to said probe for feeding thereto a high-frequency alternating waveform of limited current and limited voltage to be conducted into a patient through said operative tip of said probe after placement of said operative tip into contact with the patient, said alternating waveform having a current and a voltage so limited as to prevent damage to organic tissues while stimulating nerves to reduce or suppress pain; and
    a synchronization circuit operatively connected to at least one of said first electrical voltage source and said second electrical voltage source and having an enabling circuit component including a time delay element for enabling a commencing of probe vibration only after a predetermined time period has elapsed after a conducting of said alternating waveform into the patient has commenced.

2. The medical treatment device defined in claim 1 wherein said enabling circuit component further includes a detector operatively connected to said delay element, said detector being operatively connected to at least one of said probe and said second electrical voltage source for sensing when a conducting of said alternating waveform into the patient via said probe has commenced.

3. The medical treatment device defined in claim 1 wherein said second electrical voltage source is configured to provide said alternating waveform with a frequency between approximately 70 MHz and approximately 100 MHz.

4. The medical treatment device defined in claim 1 wherein said second electrical voltage source includes a circuit for pulsing said alternating waveform.

5. A medical treatment method comprising:
    contacting a patient with an operative tip of an ultrasonic probe;
    conducting a high-frequency alternating voltage into the patient through said operative tip of said probe while said operative tip is in contact with the patient, said alternating voltage having a current and a voltage so limited as to prevent damage to organic tissues while stimulating nerves to reduce or suppress pain; and
    mechanically vibrating said probe so that said operative tip oscillates at an ultrasonic frequency while said operative tip is in contact with the patient,
    the mechanical vibrating of said probe commencing only after a predetermined time period has elapsed after a conducting of said alternating waveform into the patient has commenced.

6. The medical treatment method defined in claim 5 wherein the enabling includes automatically detecting when a conducting of said alternating voltage into the patient via said probe has commenced.

7. The medical treatment method defined in claim 5 wherein said alternating voltage has a frequency between approximately 70 MHz and 100 MHz.

8. The medical treatment method defined in claim 5 wherein the conducting of said alternating voltage includes pulsing said alternating voltage.

* * * * *